(12) United States Patent
Marigowda

(10) Patent No.: US 9,295,500 B2
(45) Date of Patent: Mar. 29, 2016

(54) SCREW DRIVER WITH RELEASE FOR A MULTIAXIAL BONE SCREW

(71) Applicant: SPINE WAVE, INC., Shelton, CT (US)

(72) Inventor: Shresta Marigowda, Morton, PA (US)

(73) Assignee: Spine Wave, Inc., Spine Wave, CT (US)

( * ) Notice: Subject to any disclaimer, the term of this patent is extended or adjusted under 35 U.S.C. 154(b) by 344 days.

(21) Appl. No.: 13/915,686

(22) Filed: Jun. 12, 2013

(65) Prior Publication Data
US 2014/0371756 A1 Dec. 18, 2014

(51) Int. Cl.
A61B 17/58 (2006.01)
A61B 17/60 (2006.01)
A61F 2/00 (2006.01)
A61B 17/70 (2006.01)

(52) U.S. Cl.
CPC .................... A61B 17/7082 (2013.01)

(58) Field of Classification Search
CPC ............ A61B 17/7082; A61B 17/864; A61B 17/7076
USPC ....... 606/86 A, 104, 246, 264–270, 300, 301, 606/304, 306
See application file for complete search history.

(56) References Cited

U.S. PATENT DOCUMENTS

| | | |
|---|---|---|
| 2,248,054 A | 7/1941 | Becker |
| 4,238,339 A | 12/1980 | Khutoretsky et al. |
| 4,363,250 A | 12/1982 | Suga |
| 4,411,191 A | 10/1983 | Combeau |
| 4,411,259 A | 10/1983 | Drummond |
| 4,448,191 A | 5/1984 | Rodnyansky et al. |
| 4,657,001 A | 4/1987 | Fixel |
| 4,736,738 A | 4/1988 | Lipovsek et al. |
| 4,763,548 A | 8/1988 | Leibinger et al. |
| 4,913,134 A | 4/1990 | Luque |
| 5,049,151 A | 9/1991 | Durham et al. |
| 5,092,866 A | 3/1992 | Breard et al. |
| 5,139,499 A | 8/1992 | Small et al. |
| 5,242,443 A | 9/1993 | Kambin |

(Continued)

FOREIGN PATENT DOCUMENTS

FR 2510022 1/1983

OTHER PUBLICATIONS

Synthes Spine, "Constellation CP System—Technique Guide", 2003, Synthes Spine, Inc., West Chester, PA 19380.

(Continued)

Primary Examiner — Christopher Beccia
Assistant Examiner — Diana S Jones
(74) Attorney, Agent, or Firm — Hoffman & Baron, LLP

(57) ABSTRACT

A screwdriver with a release for driving a multi-axial bone screw into a vertebra of the spine includes an elongate shaft defining a driving tip at its distal end for engaging and rotating the head of the bone screw. The screw driver includes a screw engagement member affixed to the shaft for joint rotational movement therewith, the screw engagement member comprising a releasable retention member for releasable attachment to the bone screw yoke. A release member is disposed about the elongate shaft comprising a hollow grip sleeve and a hollow push sleeve joined together for common axial movement along the elongate shaft. The grip sleeve is freely rotatable about the shaft and the push sleeve is rotatable relative to the grip sleeve and engaged with a proximal portion of the shaft for joint rotational movement therewith.

15 Claims, 6 Drawing Sheets

(56) References Cited

U.S. PATENT DOCUMENTS

| | | | |
|---|---|---|---|
| 5,263,953 A | 11/1993 | Bagby | |
| 5,354,292 A | 10/1994 | Braeuer et al. | |
| 5,355,752 A | 10/1994 | Keenan et al. | |
| 5,411,503 A | 5/1995 | Hollstien et al. | |
| 5,423,819 A | 6/1995 | Small et al. | |
| 5,439,464 A | 8/1995 | Shapiro | |
| 5,458,608 A | 10/1995 | Wortrich | |
| 5,649,931 A | 7/1997 | Bryant et al. | |
| 5,667,513 A | 9/1997 | Torrie et al. | |
| 5,741,261 A | 4/1998 | Moskovitz et al. | |
| 5,814,072 A | 9/1998 | Bonutti | |
| 5,897,574 A | 4/1999 | Bonutti | |
| 5,902,231 A | 5/1999 | Foley et al. | |
| 5,910,141 A | 6/1999 | Morrison et al. | |
| 5,948,002 A | 9/1999 | Bonutti | |
| 5,954,635 A | 9/1999 | Foley et al. | |
| 5,961,538 A | 10/1999 | Pedlick et al. | |
| 5,961,554 A | 10/1999 | Janson et al. | |
| 6,090,113 A | 7/2000 | Le Couedic et al. | |
| 6,102,934 A | 8/2000 | Li | |
| 6,183,472 B1 | 2/2001 | Lutz | |
| 6,188,472 B1 | 2/2001 | Gage et al. | |
| 6,189,422 B1 | 2/2001 | Stihl | |
| 6,235,028 B1 | 5/2001 | Brumfield et al. | |
| 6,440,133 B1 | 8/2002 | Beale et al. | |
| 6,530,926 B1 | 3/2003 | Davison | |
| 6,530,929 B1 | 3/2003 | Justis et al. | |
| 6,660,006 B2 | 12/2003 | Markworth et al. | |
| D488,229 S | 4/2004 | Rinner et al. | |
| 6,716,218 B2 | 4/2004 | Holmes et al. | |
| 6,793,656 B1 | 9/2004 | Mathews | |
| 6,802,844 B2 | 10/2004 | Ferree | |
| 6,830,574 B2 | 12/2004 | Heckele et al. | |
| 6,945,933 B2 | 9/2005 | Branch et al. | |
| 7,008,422 B2 | 3/2006 | Foley et al. | |
| 7,011,660 B2 | 3/2006 | Sherman et al. | |
| 7,160,300 B2 | 1/2007 | Jackson | |
| 7,179,261 B2 * | 2/2007 | Sicvol | A61B 17/7091 606/86 A |
| 7,188,626 B2 | 3/2007 | Foley et al. | |
| 7,226,453 B2 | 6/2007 | Chao et al. | |
| 7,250,052 B2 | 7/2007 | Landry et al. | |
| 7,306,603 B2 | 12/2007 | Boehm, Jr. et al. | |
| 7,420,279 B2 | 9/2008 | Ohnishi et al. | |
| 7,465,306 B2 | 12/2008 | Pond, Jr. et al. | |
| 7,473,267 B2 | 1/2009 | Nguyen et al. | |
| 7,476,240 B2 | 1/2009 | Raymond et al. | |
| 7,491,208 B2 | 2/2009 | Pond, Jr. et al. | |
| 7,491,218 B2 | 2/2009 | Landry et al. | |
| 7,497,869 B2 | 3/2009 | Justis | |
| 7,520,879 B2 | 4/2009 | Justis et al. | |
| 7,527,638 B2 | 5/2009 | Anderson et al. | |
| 7,563,264 B2 | 7/2009 | Landry et al. | |
| 7,572,276 B2 | 8/2009 | Lim et al. | |
| 7,588,575 B2 | 9/2009 | Colleran et al. | |
| 7,588,588 B2 | 9/2009 | Spitler et al. | |
| 7,597,694 B2 | 10/2009 | Lim et al. | |
| 7,618,442 B2 | 11/2009 | Spitler et al. | |
| 7,621,918 B2 | 11/2009 | Jackson | |
| 7,648,506 B2 | 1/2010 | McCord et al. | |
| 7,648,507 B2 | 1/2010 | Techiera et al. | |
| 7,648,521 B2 | 1/2010 | Hestad | |
| 7,666,188 B2 | 2/2010 | Anderson et al. | |
| 7,666,189 B2 | 2/2010 | Gerber et al. | |
| 7,686,814 B2 | 3/2010 | Lim et al. | |
| 7,708,763 B2 | 5/2010 | Selover et al. | |
| 7,758,584 B2 | 7/2010 | Bankoski et al. | |
| 7,758,617 B2 | 7/2010 | Iott et al. | |
| 8,231,635 B2 | 7/2012 | Sharifi-Mehr et al. | |
| 8,394,108 B2 | 3/2013 | McLean et al. | |
| 2003/0208203 A1 | 11/2003 | Lim et al. | |
| 2004/0138662 A1 | 7/2004 | Landry et al. | |
| 2005/0065517 A1 | 3/2005 | Chin | |
| 2005/0080418 A1 | 4/2005 | Simonsen et al. | |
| 2005/0131422 A1 | 6/2005 | Anderson et al. | |
| 2005/0154389 A1 | 7/2005 | Selover et al. | |
| 2005/0228380 A1 | 10/2005 | Moore et al. | |
| 2005/0245928 A1 | 11/2005 | Colleran et al. | |
| 2005/0277934 A1 | 12/2005 | Vardiman | |
| 2006/0025773 A1 | 2/2006 | Yevmenenko et al. | |
| 2006/0084993 A1 | 4/2006 | Landry et al. | |
| 2006/0111714 A1 | 5/2006 | Foley | |
| 2006/0142761 A1 | 6/2006 | Landry et al. | |
| 2006/0200135 A1 | 9/2006 | Sherman et al. | |
| 2006/0229614 A1 | 10/2006 | Foley et al. | |
| 2006/0247630 A1 | 11/2006 | Iott et al. | |
| 2006/0264942 A1 | 11/2006 | Lim et al. | |
| 2006/0264962 A1 | 11/2006 | Chin et al. | |
| 2006/0276803 A1 | 12/2006 | Salerni | |
| 2006/0293693 A1 | 12/2006 | Farr et al. | |
| 2007/0016188 A1 | 1/2007 | Boehm, Jr. et al. | |
| 2007/0016198 A1 | 1/2007 | Boehm, Jr. et al. | |
| 2007/0016199 A1 | 1/2007 | Boehm, Jr. et al. | |
| 2007/0078460 A1 | 4/2007 | Frigg et al. | |
| 2007/0167954 A1 | 7/2007 | Sievol et al. | |
| 2007/0173745 A1 | 7/2007 | Diederich et al. | |
| 2007/0185491 A1 | 8/2007 | Foley et al. | |
| 2007/0198015 A1 | 8/2007 | Foley et al. | |
| 2007/0233097 A1 | 10/2007 | Anderson et al. | |
| 2008/0009864 A1 | 1/2008 | Forton et al. | |
| 2008/0039838 A1 | 2/2008 | Landry et al. | |
| 2008/0045970 A1 | 2/2008 | Saidha et al. | |
| 2008/0051787 A1 | 2/2008 | Remington et al. | |
| 2008/0077135 A1 | 3/2008 | Stad et al. | |
| 2008/0077139 A1 | 3/2008 | Landry et al. | |
| 2008/0119858 A1 | 5/2008 | Potash | |
| 2008/0125788 A1 | 5/2008 | Cohen et al. | |
| 2008/0200918 A1 | 8/2008 | Spitler et al. | |
| 2008/0208258 A1 | 8/2008 | Foley et al. | |
| 2008/0221583 A1 | 9/2008 | Sharifi-Mehr et al. | |
| 2008/0243133 A1 | 10/2008 | Heinz | |
| 2008/0312703 A1 | 12/2008 | Hestad et al. | |
| 2009/0005814 A1 | 1/2009 | Miller et al. | |
| 2009/0082666 A1 | 3/2009 | Geist et al. | |
| 2009/0082811 A1 | 3/2009 | Stad et al. | |
| 2009/0099172 A1 | 4/2009 | Cai et al. | |
| 2009/0105774 A1 | 4/2009 | Jones et al. | |
| 2009/0138056 A1 | 5/2009 | Anderson et al. | |
| 2009/0143828 A1 * | 6/2009 | Stad et al. | 606/86 A |
| 2009/0182382 A1 | 7/2009 | Justis et al. | |
| 2009/0264895 A1 | 10/2009 | Gasperut et al. | |
| 2009/0264930 A1 | 10/2009 | McBride | |
| 2009/0312797 A1 | 12/2009 | Lim et al. | |
| 2010/0004695 A1 | 1/2010 | Stad et al. | |
| 2010/0024487 A1 | 2/2010 | Khoo et al. | |
| 2010/0030283 A1 | 2/2010 | King et al. | |
| 2010/0036443 A1 | 2/2010 | Hutton et al. | |
| 2010/0069972 A1 | 3/2010 | Jones et al. | |
| 2010/0094359 A1 | 4/2010 | Techiera et al. | |
| 2010/0137915 A1 | 6/2010 | Anderson et al. | |
| 2010/0145348 A1 | 6/2010 | Marino | |
| 2010/0145349 A1 | 6/2010 | Lim et al. | |
| 2010/0145389 A1 | 6/2010 | Triplett et al. | |
| 2010/0174326 A1 | 7/2010 | Selover et al. | |
| 2010/0198272 A1 | 8/2010 | Keyer et al. | |
| 2011/0313471 A1 * | 12/2011 | McLean | A61B 17/7082 606/305 |

OTHER PUBLICATIONS

Synthes Spine, "Cannulated Pangea System—Technique Guide", 2007, Synthes Spine, Inc., West Chester, PA 19380.

Peterson, M.D., Mark et al; "NuVasive Creative Spine Technology, Spherx DBR Surgical Technique", 2005, NuVasive, Inc., San Diego, CA 92121.

Abbott, "PathFinder, Minimally Invasive Pedicle Screw System, Surgical Technique", Oct. 2008, 1199-0005-MKC Rev H per DCR 6005, Abbott Spine, Austin, Texas 78727.

Foley, M.D., Kevin T., Medtronic Sofamor Danek, "CD Horizon Sextant Rod Insertion System Surgical Technique, Minimal Access Spinal Technologies", 2002, Medtronic Sofamor Danek USA, Memphis, TN 38132.

(56) References Cited

OTHER PUBLICATIONS

Anderson, M.D., D. Greg et al; "DePuySpine, Viper 2 Expedum System Guide", May 2008, MIO4-03-000, JC/UM, DePuySpine, Raynham, MA 02767.

Biomet Spine, Ballista Percutaneous Screw Placement System—Surgical Technique, 2008, Biomet, Inc., Parsippany, NJ 07054.

International Search Report and Written Opinion of the International Searching Authority issued in counterpart PCT Application No. PCT/US2012/037916 dated Aug. 8, 2012.

\* cited by examiner

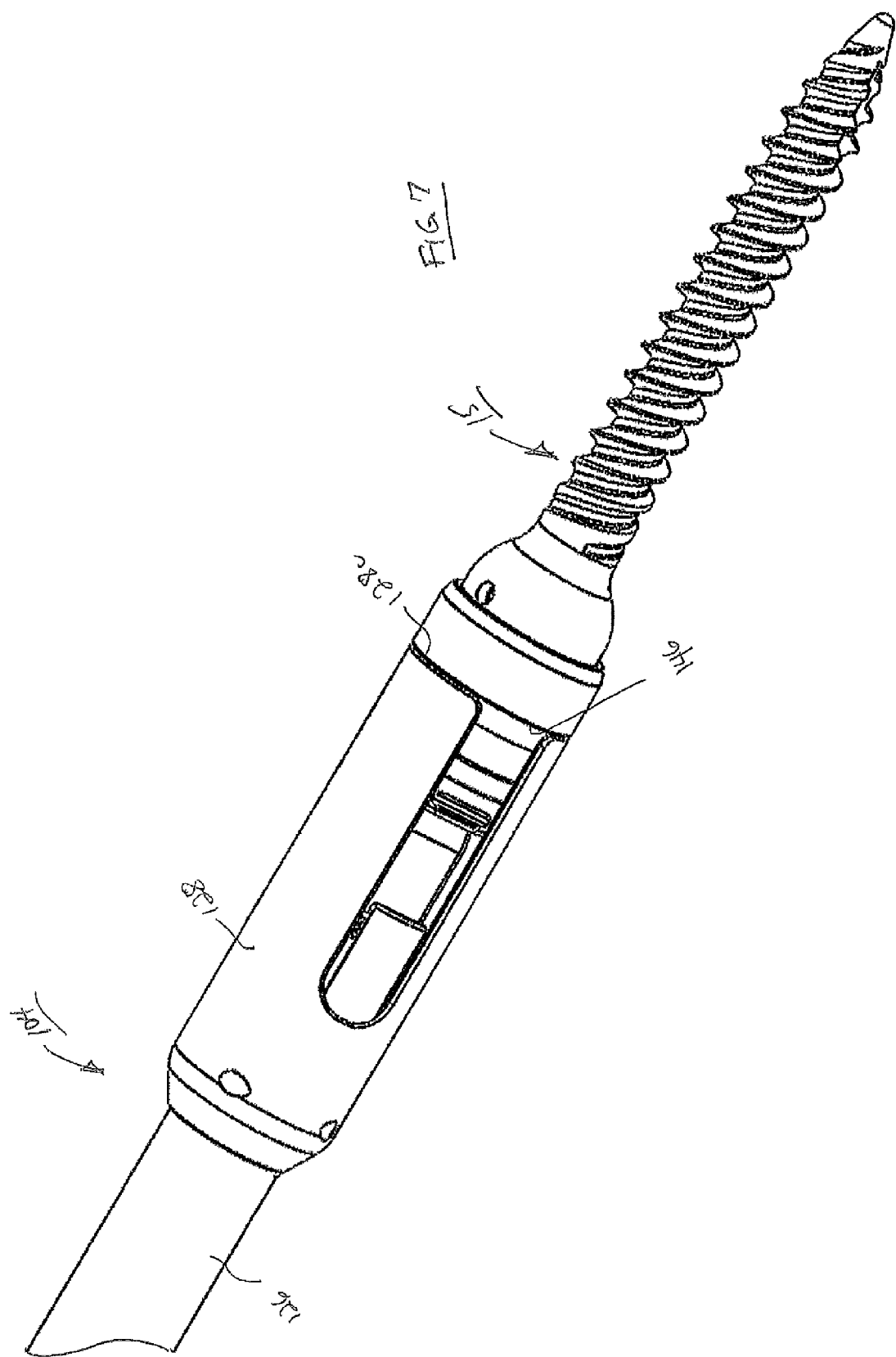

SCREW DRIVER WITH RELEASE FOR A MULTIAXIAL BONE SCREW

BACKGROUND

The present disclosure contemplates instrumentation and procedures for achieving spinal fixation and more particularly to a screw driver with a release for driving a bone screw into a vertebra of a patient.

A typical spinal fixation system 10 as shown in FIG. 1 spans between successive vertebrae V of the spine. An elongated member, such as rod 12, extends along the length of the spine and provides an anchor point for connecting each vertebra to the rod. The rod is typically contoured to approximate the normal curvature of the spine for the particular instrumented spinal segments, which may include lordosis or kyphosis. Anchor devices 15 are provided for connecting the vertebral segments to the elongated member. These anchor devices may include hooks, bolts, screws or other means for engaging a vertebra. For the purposes of the present discussion, the anchor device 15 is a bone screw assembly, such as the screw assembly shown in FIG. 2.

The bone engaging fastener or screw assembly 15 includes a shank 16 that carries threads configured to engage vertebral bone. For instance, the fastener is a multi-axial pedicle screw with a shank that is threaded for engagement within the pedicle of the vertebra. The screw assembly further includes a head 16a by which the screw, and ultimately the vertebra, is fastened to the spinal rod 12. In particular, the head 16a supports a yoke 17 that is generally U-shaped to receive the spinal rod therethrough, as depicted in FIG. 2. The rod 12 may be supported in part by a collar 18 mounted over the head 16a of the bone screw. A cap 19 may carry a set screw 20 that locks the rod within the yoke 17 and thus fastens the rod 12 to the bone screw or the set screw 20 may be threadably attached directly to the yoke 17. In the multi-axial bone screw assembly 15 the yoke 17 is articulatingly attached to the threaded bone screw 16, and more specifically to the head 16a of the bone screw, so that the yoke 17 can adopt a range of spherical angles relative to the bone screw. Thus, the yoke can articulate relative to the bone screw fastened in the vertebra so that the slot 42 can be aligned to receive the connecting rod 25.

While in the past spinal fixation systems using multi-axial screws have been implanted in open procedures involving relatively large incisions through the patient's tissue with significant muscle retraction, more recent procedures have been developed to introduce spinal fixation systems in a minimally invasive or percutaneous manner. A screw driver for use in implanting multi-axial bone screws is such procedures is shown and described in commonly-assigned U.S. Pat. No. 8,394,108, issued on Mar. 12, 2013 to Scott McLean and Stephen Seyer, (hereinafter "the 108 Patent"), the disclosure of which is incorporated herein by reference in its entirety. While the screw driver of the '108 Patent is an improvement in the art, it is also desirable to provide further features that aid the surgeon in readily releasing the screw driver instrument from the bone screw after implantation.

SUMMARY

An object of the present invention is to provide a screw driver with a release for driving a multi-axial bone screw into a vertebra of the spine and for removing the screwdriver from the implanted bone screw.

DESCRIPTION OF THE FIGURES

FIG. 7 is a further view of FIG. 6 with the push sleeve axially moved into contact with the upper shoulder of the bone screw.

DETAILED DESCRIPTION

Figure 2:
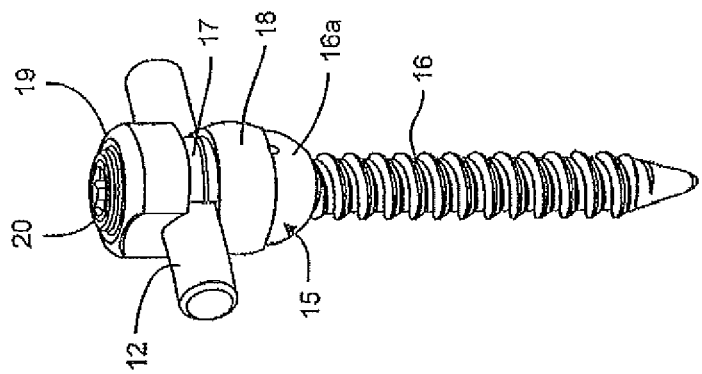
FIG. 2 is a perspective view of a bone engaging fastener in the form of a multi-axial pedicle screw suitable for use with a procedure disclosed herein.
Figure 1:
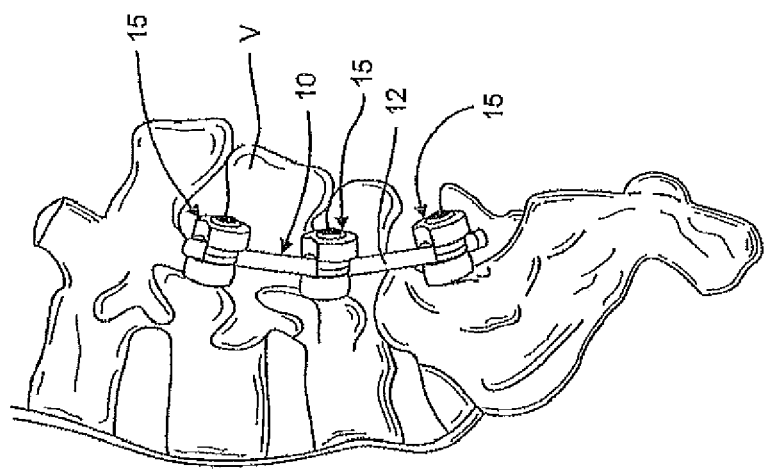
FIG. 1 is a representation of a portion of a patient's spine instrumented with a multi-level fixation system.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 3:
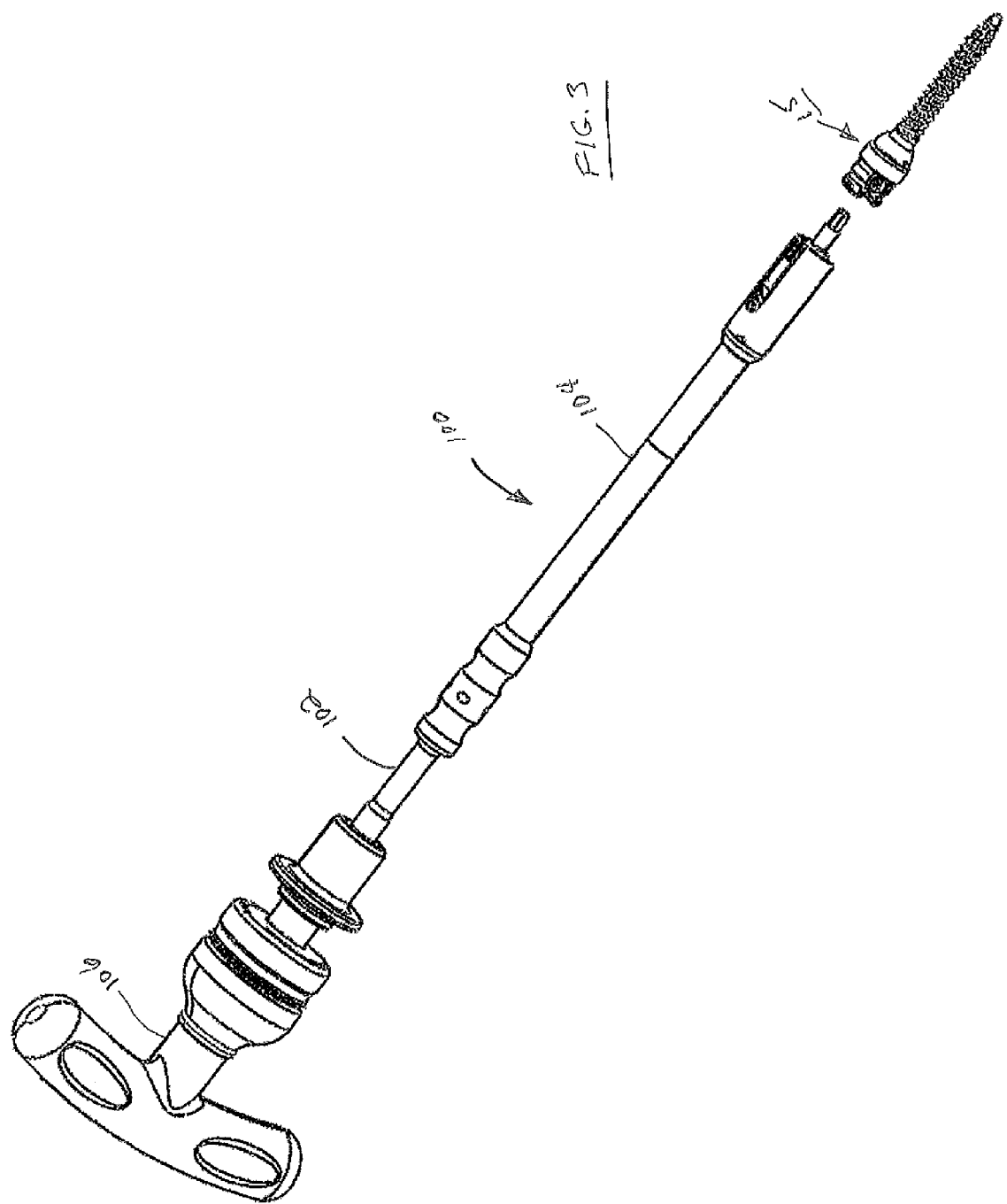
FIG. 3 is a perspective exploded view of a screw driver in accordance with one arrangement of the invention and a multi-axial bone screw.
Figure 4:
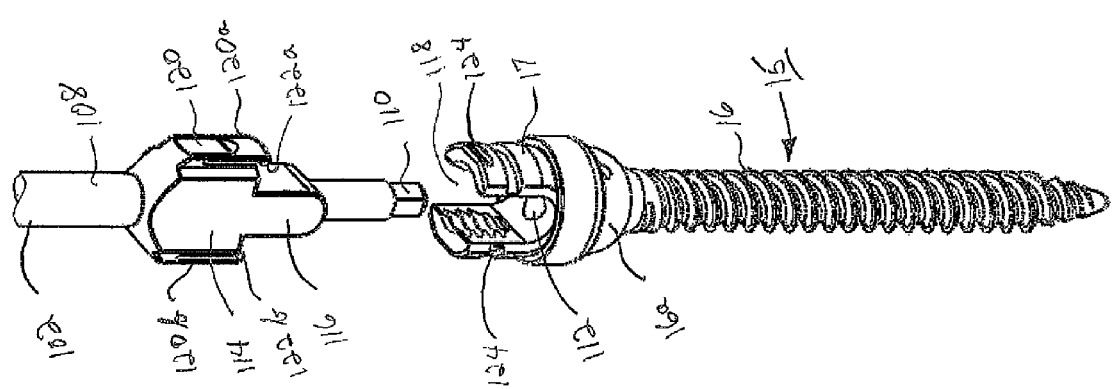
FIG. 4 is an exploded enlarged perspective view of the proximal end of the screw driver showing details of the screw engagement member and the multi-axial bone screw of FIG. 3.

By reference also to FIGS. 3-4, a screw driver 100 with a release is shown in exploded relation with multi-axial bone screw 15. Screw driver 100 comprises a driver 102, a sleeve assembly 104 and a handle 106 suitably attached to driver 102 at the proximal end thereof. As illustrated in FIG. 4, the distal end of driver 102 is configured in a manner particularly useful for insertion of a multi-axial bone screw in an open spinal procedure as described in the '108 Patent with reference to FIGS. 8-9 thereof. Driver 102 comprises an elongate shaft 108 which includes at the distal end a tip defining an engagement end 110 that is configured to engage a drive tool recess 112 in the base of the bone screw head 16a. The engagement end 110 and drive tool recess 112 can be configured in a conventional manner to be a hex or Torx feature. The shaft 108 of screw driver 100 is sized and of length so that the engagement end 110 can be received within the recess 112 while handle 106 is accessible at the proximal end outside the patient.

The screw driver 100 includes adjacent the distal end of the shaft 108 and spaced proximally from 110 an engagement member 114. Engagement member 114 is affixed to the elongate shaft 108 for joint rotational movement therewith. Engagement member 114 includes at its distal end a stop 116 that is shaped and configured to seat within a slot 118 of the yoke 17. Stop 116 is configured to rotate the yoke 17 upon rotation of the shaft 108 as engagement end 110 drives the threaded shank 16 into a pedicle of a vertebra.

Engagement member 114 includes a releasable retention member 120 for releasable attachment to the yoke 17. Releasable retention member 120 comprises a pair of flexible elements 120a and 120b. Flexible elements 120a and 120b are preferably cantilevered spring elements each having an inward projection 122a and 122b at the free ends thereof. Inward projections 122a and 122b are formed to provide an inward bias for extending releasably into the slots 124 in the exterior surfaces of arms of yoke 17. As such, flexible elements 120a and 120b attach releasably to the outside of the yoke 17 and may provide an audible click on such attachment. While the screw driver 100 has been described particularly with a configuration useful for insertion of a multi-axial bone screw in an open spinal procedure, it should be appreciated that the screw driver of the subject invention may also be configured for use in other procedures such as those described in the '108 Patent where the flexible elements 120a and 120b may be configured to provide an outward bias for releasable connection to interior surfaces of the yoke 17.

Figure 5:
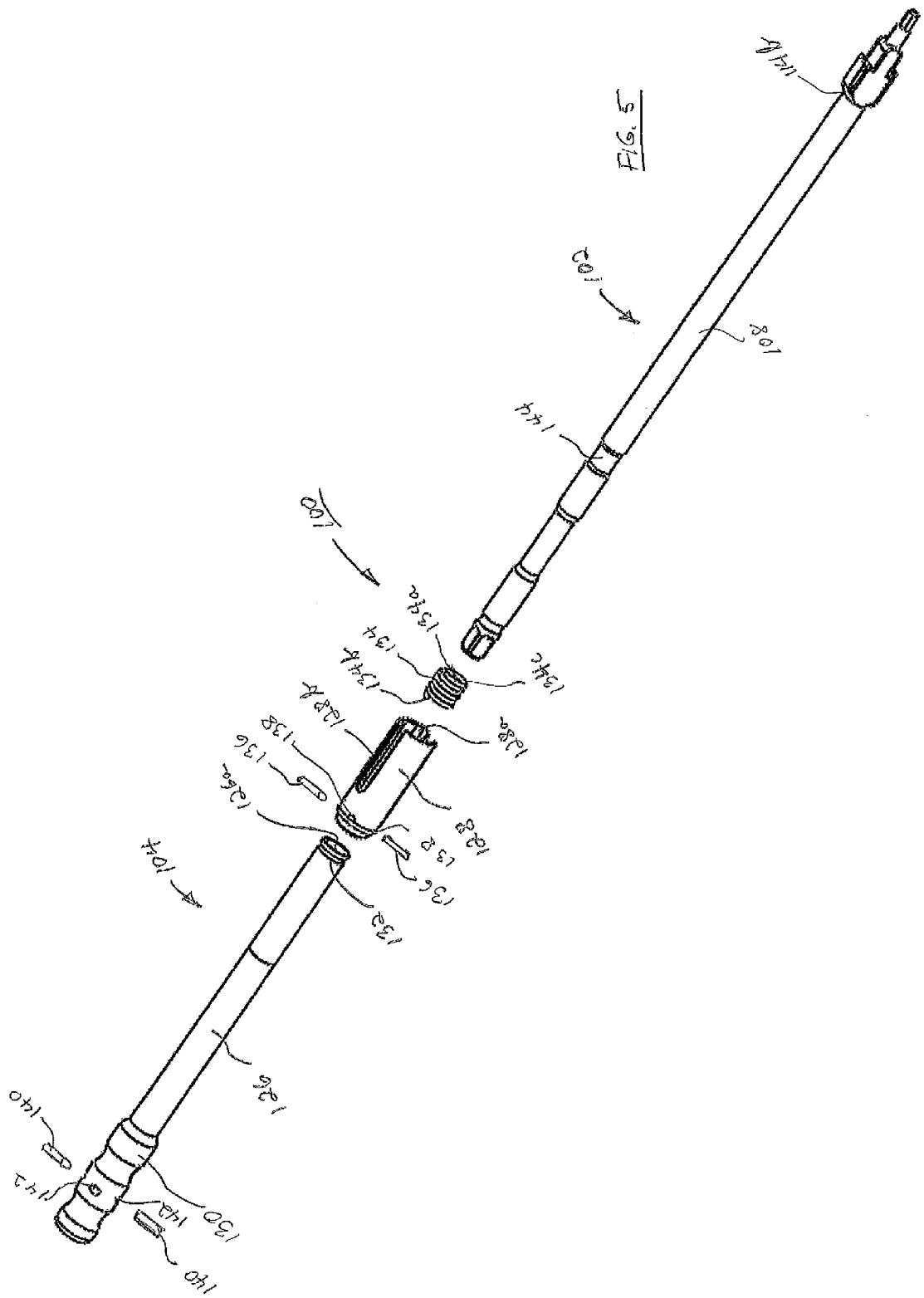
FIG. 5 is an exploded perspective view of the screw driver of FIG. 3 showing the elongate driver and the release member.

Turning now to FIG. 5, further details of the sleeve assembly 104 are described. Sleeve assembly 104 is a release member for the screw driver 100 and comprises an elongate hollow grip sleeve 126 and an elongate hollow push sleeve 128 rotatably attached thereto. Grip sleeve 126 has a lumen 126a extending lengthwise therethrough. Lumen 126a is sized and configured to slidably receive therethrough elongate shaft 108 of driver 102. Grip sleeve 126 includes a grip portion 130 at the proximal end thereof and a slot 132 extending fully circumferentially around the distal end thereof.

Push sleeve 128 has a lumen 128a extending therethrough for communication with the lumen 126a of said grip sleeve 126. Push sleeve has a pair of opposing elongate slots 128b opening at the distal end thereof and extending lengthwise through the walls of the push sleeve 128 for a length toward the closed proximal end. A spring element such as a helical spring 134 is configured to be disposed within the lumen 128a of grip sleeve 128. Spring 134 has an internal opening 134a sized and configured to slide over elongate shaft 108 of driver 102. The proximal end 134b of spring 134 is suitably retained within the lumen 128a of grip sleeve 128 such as by an internal slot in the interior surface of grip sleeve 128. The distal end 134c is configured to engage an upper surface 114b, as will be described.

The grip sleeve 126, push sleeve 128 and the driver 102 are assembled as follows with continued reference to FIG. 5. The push sleeve 128 is pinned to the grip sleeve 126 by a pair of pins 136 extending through a complementary pair of openings 138 extending through the proximal end of the push sleeve 128. Pins 136 are received through openings 138 and extend into the circumferential slot 132 formed at the distal end of grip sleeve 126. The axial extent of slot 132 is formed to be slightly greater than the diameter of pins 136, thereby allowing full circumferential rotation of the push sleeve 128 relative to the grip sleeve 126 while allowing substantially no axial movement. As such, grip sleeve 126 and push sleeve 128 are joined for substantial common axial movement. With spring 134 being retained in push sleeve 128, spring 134 similarly moves axially in common with grip sleeve 126 and push sleeve 128. It should be appreciated that while a pair of pins 136 is described, the number of pins may be fewer or greater.

Elongate shaft 108 is then slidably received through the opening 134a of spring 134 and through the lumens 128a and 126a of push sleeve 128 and grip sleeve 126, respectively. The grip sleeve 126 is pinned to the elongate shaft 108 by a pair of pins 140 extending through a complementary pair of openings 142 extending through the proximal end of the grip sleeve 126. Pins 140 are received through openings 142 and extend into a circumferential elongated slot 144 formed around elongate shaft 108. The axial extent of slot 144 is formed to be of length greater than the diameter of pins 140, such as greater than at least two times the diameter of the pin 140, thereby allowing a certain extent of axial movement of the pins 140 within elongated slot 144. Thus, grip sleeve 126 can move a limited amount axially relative to elongate shaft 108 as well as rotate fully circumferentially relative to the elongate shaft 108. Again, it should be appreciated that while a pair of pins 140 is described, the number of pins may be fewer or greater.

Figure 6:
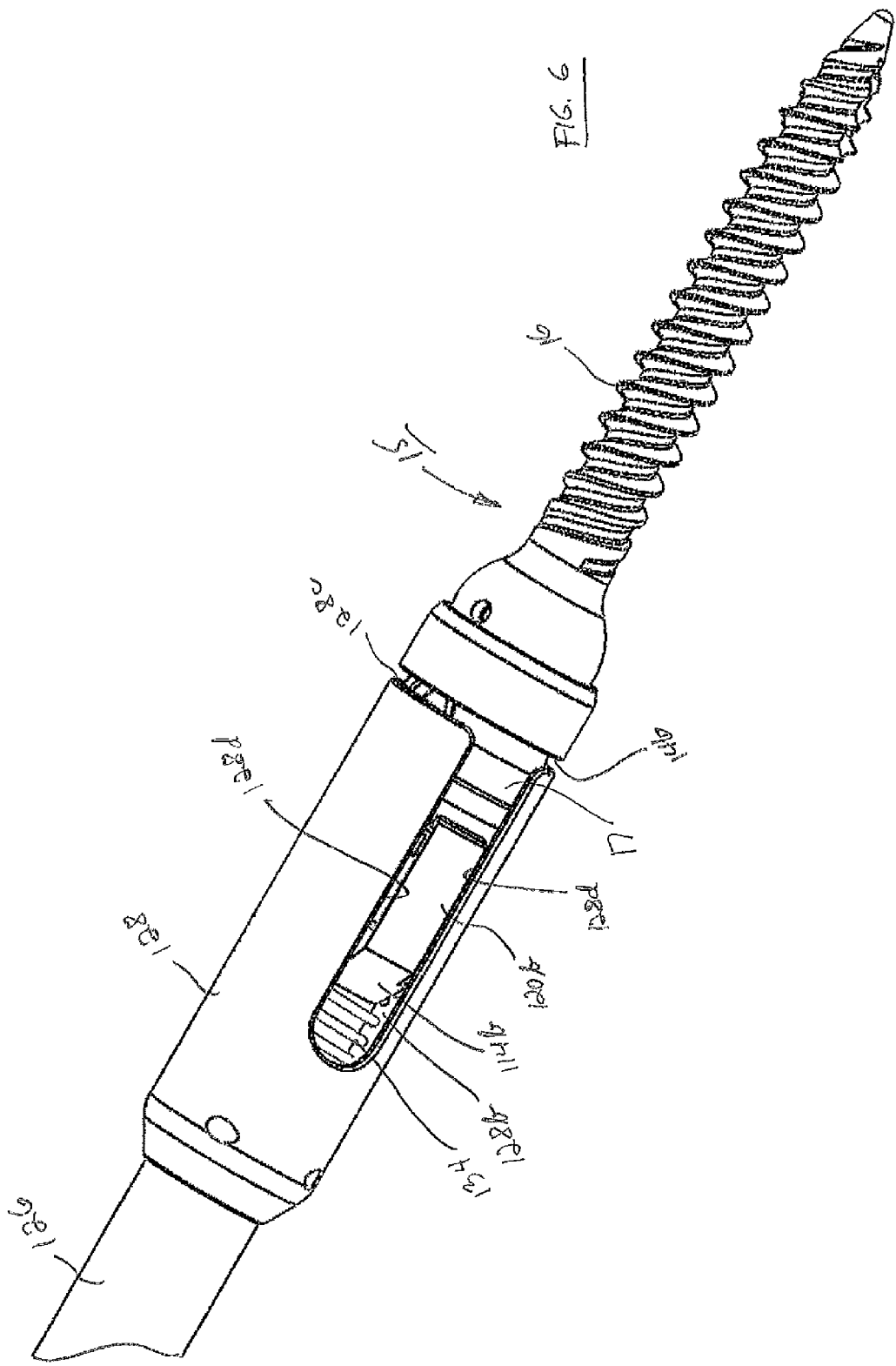
FIG. 6 is an enlarged perspective view of the screw driver of FIG. 3 attached to the bone screw with the push sleeve of the release member being disposed about the yoke and spaced from an upper shoulder of the bone screw.

Turning now to FIGS. 6-7 the use of the screw driver 100 as assembled is described. The engagement member 114 at the distal end of driver 102 is releasably attached to the yoke 17 of multi-axial screw 15 by snapping flexible elements 120a and 120b into slots 124 in the exterior surfaces of the yoke arms. Flexible elements 120a and 120b are received within respective opposing slots 128b of push sleeve 128. The engagement end 110 of driver 102 is received in recess 112 as described above while stop 116 is seated within slot 118 of the yoke 17 (FIG. 4). Spring 134 contained within push sleeve 128 is disposed with proximal end 134c in contact with upper surface 114b of engagement member 114. At this stage, spring 134 which is not compressed, will keep the distal edge 128c of push sleeve 128 axially spaced a short distance from an upper facing shoulder 146 of multi-axial bone screw 15, as depicted in FIG. 6. The push sleeve 128 will, however, substantially surround yoke 17 as well as engagement member 114 so as to reduce cutting or scraping of tissue as multi-axial screw 15 with engagement member 114 is rotated. Side edges 128d of opposing slots 128b are spaced to be in close proximity to the side edges of the flexible elements 120a and 120b. Accordingly, the surgeon may threadably insert a multi-axial screw 15 into a vertebra by rotation of elongate shaft 108 through rotation of handle 106. During such rotation, the surgeon may grasp grip sleeve 126 which will remain stationary while the elongate shaft 108 rotates the engagement member 114 for rotating multi-axial screw 15. As engagement member 114 rotates, the side edges 128d of slots 128b will engage the flexible elements 120a and 120b thereby rotating push sleeve 128 together with engagement member 114 relative to grip sleeve 126, which remains stationary in the surgeon's grasp.

Once multi-axial screw 15 is properly seated within a vertebra, the screw driver 100 may be removed therefrom. With reference to FIG. 7 the sleeve assembly 104 of the screw driver 100 is moved axially proximally as allowed by the axial movement of pins 140 within elongated slot 144 until the distal edge 128c of push sleeve 128 is placed in contact with upper facing shoulder 146 as spring 134 is compressed. While the surgeon holds sleeve assembly 104 against upper facing shoulder 146 of multi-axial screw 15 the surgeon then pulls the elongate shaft 108 proximally to thereby provide sufficient force to overcome the releasable engagement of the flexible elements 120a and 120b with the yoke 17, thereby releasing the screw driver 100 from a multi-axial screw 15. Such release of the screw driver 100 releases the compression on spring 134. It should be appreciated that the sleeve assembly 104 provides a counter force against the force needed to separate the screw driver 100 from the bone screw 15, thereby easing the separation while reducing those forces tending to pullout the inserted bone screw.

Having described the particular arrangement of the screw driver 100, it should be appreciated that variations may be made thereto. For example, the sleeve assembly 104 described with reference to FIG. 5 hereinabove, may be used as a separate instrument without being pinned to the elongate shaft 108 for removal and release of screw drivers without release features, such as those described in the '108 Patent. In such an application, the sleeve assembly 104 may be placed over the elongate shaft of the screw driver and freely move rotationally and axially thereon.

While the invention has been illustrated and described in detail in the drawings and foregoing description, the same should be considered as illustrative and not restrictive in character. For example, while the screws 15 are multi-axial screws, the screw driver 100 as described herein may be used also with mono-axial screws as well as in procedures to drive screws into a bone of a patient other than the spine. It is understood that only the preferred embodiments have been presented and that all changes, modifications and further applications that come within the spirit of the invention are desired to be protected.

What is claimed is:

1. A screw driver with a release for driving a bone screw into a bone of a patient, the bone screw including an elongate shaft having a threaded screw portion at the distal end and a screw head at the proximal end, said screw head having a recess therewithin, said screw driver comprising:

an elongate shaft having a distal end and a proximal end, said shaft defining a driving tip at said distal end configured to engage the recess within the screw head for rotation thereof;

a screw engagement member affixed to said shaft for joint rotational movement therewith, said screw engagement member comprising a releasable retention member for releasable attachment to bone screw; and a release member disposed about said elongate shaft comprising a hollow elongate grip sleeve and a hollow elongate push sleeve joined together for common axial movement along said elongate shaft, said grip sleeve being freely rotatable about said elongate shaft, and said push sleeve being rotatable relative to said grip sleeve and engaged with said engagement member for joint rotational movement therewith.

2. The screw driver of claim 1, wherein said grip sleeve is affixed to said elongate shaft for limited axial movement thereon.

3. The screw driver of claim 2, wherein said push sleeve is affixed to said grip sleeve for rotational movement relative thereto.

4. The screw driver of claim 3, wherein said push sleeve is affixed to said grip sleeve for substantially no axial movement relative thereto.

5. The screw driver of claim 4, wherein said push sleeve has at least one slot opening at the distal end thereof and extending lengthwise a distance toward the proximal end, said at least one slot receiving a portion of the engagement member therewithin.

6. The screw driver of claim 5, wherein said at least one slot receives said releasable retention member.

7. The screw driver of claim 6, wherein an edge of said at least one slot engages said releasable retention member.

8. The screw driver of claim 1, further comprising a spring retained within an interior of said push sleeve and in contact with a surface of said engagement member.

9. A screw driver with a release for driving a multi-axial bone screw into a vertebra of a spine, the bone screw including an elongate shaft having a threaded screw portion at the distal end and a screw head at the proximal end, and a yoke articulatingly attached to the screw head, the yoke having a slot therethrough for receiving a connecting rod, the yoke having screw head having a recess therewithin, said screw driver comprising:

an elongate shaft having a distal end and a proximal end, said shaft defining a driving tip at said distal end configured to engage the recess within the screw head for rotation thereof;

a screw engagement member affixed to said shaft for joint rotational movement therewith, said screw engagement member comprising a releasable retention member for releasable attachment to said yoke; and a release member disposed about said elongate shaft comprising a hollow elongate grip sleeve and a hollow elongate push sleeve joined together for common axial movement along said elongate shaft, said grip sleeve being freely rotatable about said elongate shaft and said push sleeve being rotatable relative to said grip sleeve and engaged with a proximal portion of said elongate shaft for joint rotational movement therewith.

10. The screw driver of claim 9, wherein said release member comprises a spring disposed between an upper surface of said engagement member and an interior surface of said push sleeve.

11. The screw driver of claim 9, wherein said elongate shaft has an elongate slot extending circumferentially around said elongate shaft adjacent the distal end, said slot having an axial length, said grip sleeve comprising a pin received in said slot for full movement of said pin circumferentially therewithin and axial movement over the axial length of said slot.

12. The screw driver of claim 11, wherein said grip sleeve has a slot extending circumferentially around a distal end thereof, said push sleeve comprising a pin received in said slot of said grip sleeve for full movement of said pin circumferentially therewithin and substantially no axial movement.

13. The screw driver of claim 9, wherein said screw engagement member comprises a stop sized to seat within the slot of said yoke and configured to rotate said yoke upon rotation of said elongate shaft, and wherein said push sleeve comprises an engagement surface in engagement with said stop for joint rotational movement with said stop.

14. The screw driver of claim 13, wherein said engagement surface of said push sleeve is an axially extending side edge of at least one slot opening at the proximal end of said push sleeve and extending lengthwise toward the proximal end thereof.

15. The screwdriver of claim 9, wherein said releasable retention member comprises a pair of flexible elements releasably attachable to said yoke, at least one of said flexible elements being received in said at least one slot.

\* \* \* \* \*